(12) United States Patent
Jones (10) Patent No.: US 9,658,333 B1
(45) Date of Patent: May 23, 2017

(54) HEIGHT MEASURING DEVICE

(71) Applicant: Mark Conrad Jones, Austin, TX (US)

(72) Inventor: Mark Conrad Jones, Austin, TX (US)

( * ) Notice: Subject to any disclaimer, the term of this patent is extended or adjusted under 35 U.S.C. 154(b) by 0 days.

(21) Appl. No.: 15/019,905

(22) Filed: Feb. 9, 2016

(51) Int. Cl.
| | |
|---|---|
| *G01P 3/36* | (2006.01) |
| *G01S 17/02* | (2006.01) |
| *G01C 9/24* | (2006.01) |
| *G01S 7/51* | (2006.01) |
| *G01S 7/497* | (2006.01) |

(52) U.S. Cl.
CPC ............... *G01S 17/02* (2013.01); *G01C 9/24* (2013.01); *G01S 7/497* (2013.01); *G01S 7/51* (2013.01)

(58) Field of Classification Search
CPC . G01S 17/02; G01S 7/497; G01S 7/51; G01C 9/24
See application file for complete search history.

(56) References Cited

U.S. PATENT DOCUMENTS

| | | | |
|---|---|---|---|
| 5,813,132 A * | 9/1998 | Bodkin, Sr. ............ | G01B 5/061 33/494 |
| 6,073,359 A | 6/2000 | Lee | |
| 6,226,881 B1 | 5/2001 | Landauer | |
| 7,987,612 B2 | 8/2011 | Hong | |
| 8,015,723 B2 | 9/2011 | Solomon | |
| 8,539,690 B2 | 9/2013 | Haykeen | |
| 8,869,415 B1 | 10/2014 | Haykeen | |
| 2005/0128465 A1 * | 6/2005 | Skultety-Betz .......... | G01C 3/08 356/4.01 |
| 2006/0265896 A1 * | 11/2006 | Kavana ................ | A61B 5/1072 33/832 |
| 2015/0219432 A1 * | 8/2015 | Liu ...................... | A61B 5/1072 33/512 |

* cited by examiner

*Primary Examiner* — Samantha K Abraham (57) ABSTRACT

An apparatus, system, and method for measuring height of one or more objects/users. Once the height-measuring device is calibrated, a retracting foot platform is positioned atop a user/object and its distance is captured, stored, and calculated by a laser sensor to determine the resulting heights of the objects/users. The height measurements may be displayed on a screen, including the screen display of the height-measuring device itself, or other devices such as a tablet, smartphone, or scale.

The height data from each user/object may be compared to one another. The height measuring device also includes a predictive algorithm that determines the future height of one or more user.

6 Claims, 6 Drawing Sheets

FIG. 6

HEIGHT MEASURING DEVICE

CROSS-REFERENCE TO RELATED APPLICATION

The present application is related to U.S. patent application also entitled "Height Measuring Device" filed simultaneously. This application is related by subject matter to that disclosed in the commonly owned, and simultaneously-filed application.

BACKGROUND

Field of the Disclosure

This invention relates to an apparatus and method for measuring height. ratus and method for measuring height.

Background of the Disclosure

Height measurement devices have evolved over the years. Traditionally, a person's height is either taken with a limp tape measure at home or at the doctor's office using a bulky, oversized height scale, typically having a floor base. Other wall mounted devices use a long cumbersome graduated rod having a sliding plank, or a basic graduated retractable tape having a hard to read parallax sight, and a plank.

Several additional electronic measurement devices have been introduced over the past decades to capture height measurements. Some devices electronically track the vertical position of a person and report the corresponding height measurement, by physically placing a device on top of a person's head, calculating the person's height by measuring the distance from the floor to the ceiling, and then subtracting the distance from the person's head to the ceiling. However, this requires a clear line of sight to a non-vaulted ceiling, and a floor. Due to the ability of the device sliding off the person's head, it has a higher probability of improperly calculating the person's height.

However, this current height-measuring device provides more stability by being mounted onto a surface, not balancing atop of a user's head, and not needing to be located at a prescribed distance from the floor. Further, it does not rely on a bulky floor base apparatus to measure height and there is no parallax error in the reading of its measurements. It provides a more efficient and accurate height measurement through the incorporation of a distance sensor, such as a laser, that calculates heights via the difference of a calibration reading from a distance reading, and it is triggered when a foot platform is moved to a different position.

BRIEF SUMMARY

An apparatus, method, and system for measuring height are provided. The apparatus, and method includes initiating, and calibrating a height-measuring device, by engaging a distance sensor to capture and store the calibration reading. The distance sensor may be in the form of a laser or other line-of-sight device. A foot platform, connected to a retractable tape, is pulled atop an object/user. A reading is captured and is used as the distance reading. The distance sensor captures, stores and calculates a height measurement for the user/object, and displays the height measurement on a screen. stores and calculates a height measurement for the user/object, and displays the height measurement on a screen.

The system includes processor instructions that are capable of capturing, calculating, and storing calibration data as well as height measuring data for one or more objects, including users. It then displays calculated height results of the objects/users. Further, the height data can be compared for more than one object/user. The height data may also be processed using a predictive algorithm in order to predict future heights of one or more user. The height measurements, including compared heights, and predicted heights may be stored, and displayed on any plurality of screens, including smartphones, scales, tablets, and the like.

This summary is provided to introduce a selection of concepts in a simplified form that are further described in the detailed description. This summary is not intended to identify key features or essential features of the claimed subject matter, nor is it intended to be used to limit the scope of the claimed subject matter.

BRIEF DESCRIPTION OF THE DRAWINGS

The invention is illustrated by the following non-limiting drawings in which.

DETAILED DESCRIPTION

Figure 1:
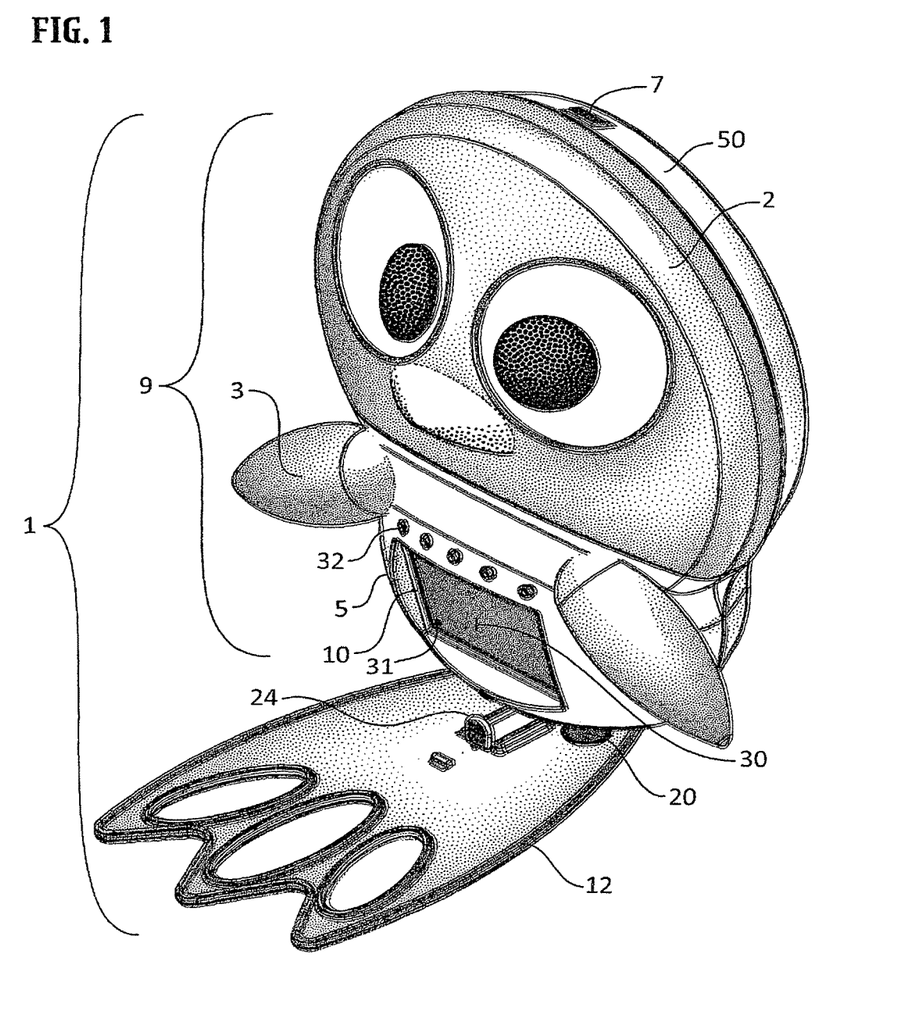
FIG. 1 is a front perspective view of a height-measuring device.

FIG. 1 depicts a height-measuring device [1] comprising a housing having a front shell assembly [9] and corresponding rear-facing shell [50]. The front shell assembly [9] in the preferred decorative embodiment includes a head [2] having a molded snap tab [7], a belly [5] having a display aperture [10], a screen display [30] having an integrated camera [31], at least one manual pushbutton [32], and decorative arms [3]. However, the front shell assembly [9] is not limited to having any decorative façade features and may be purely functional in design. The foot platform [12], having a slider tab [24] shown in a closed position, perpendicularly abuts the underside of the belly [5] and the bottom of the rear-facing shell [50] of the housing. The foot platform [12] preferably includes one or more bumpers [20] to prevent the foot platform [12] from directly contacting and damaging the underside of the housing. The foot platform [12] may include a decorative design, such as molded toe cutouts to heighten user experience.

Figure 2:
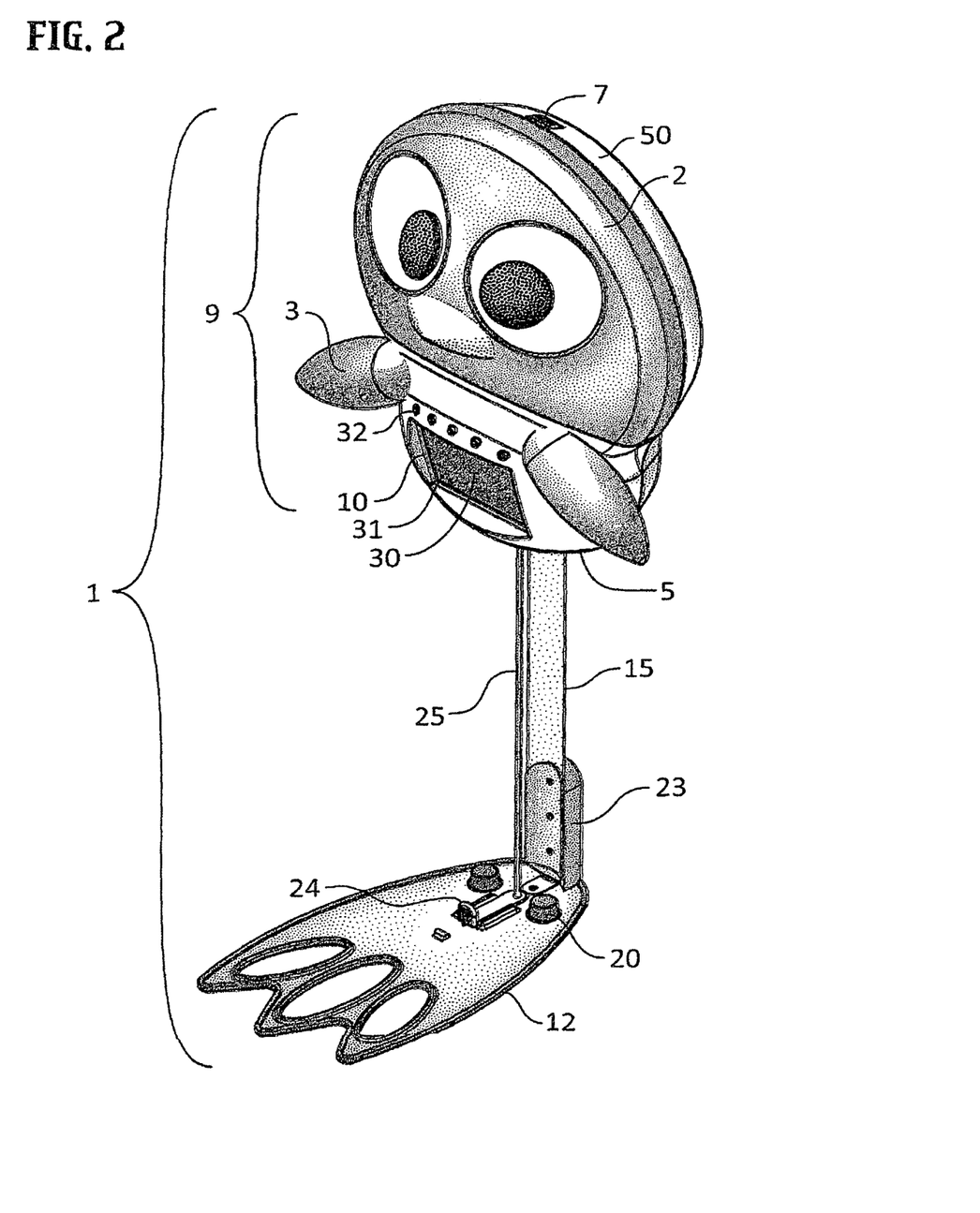
FIG. 2 is an isometric view of the height-measuring device with the foot in an extended position.

FIG. 2. depicts the height-measuring device [1] with the foot platform [12] in a partially extended position. The foot platform [12] is connected to a retractable tape [15] and is affixed by a foot bracket [23] or other attachment. In a preferred embodiment, the retractable tape [15] has similar form and structure to that of a spring-loaded tape measure. In this view, a laser beam [25] is capable of projecting in a vertical downward manner from the underside of the shell assembly [9] towards the foot platform [12], namely onto the slider tab [24] being in a closed position.

Figure 3:
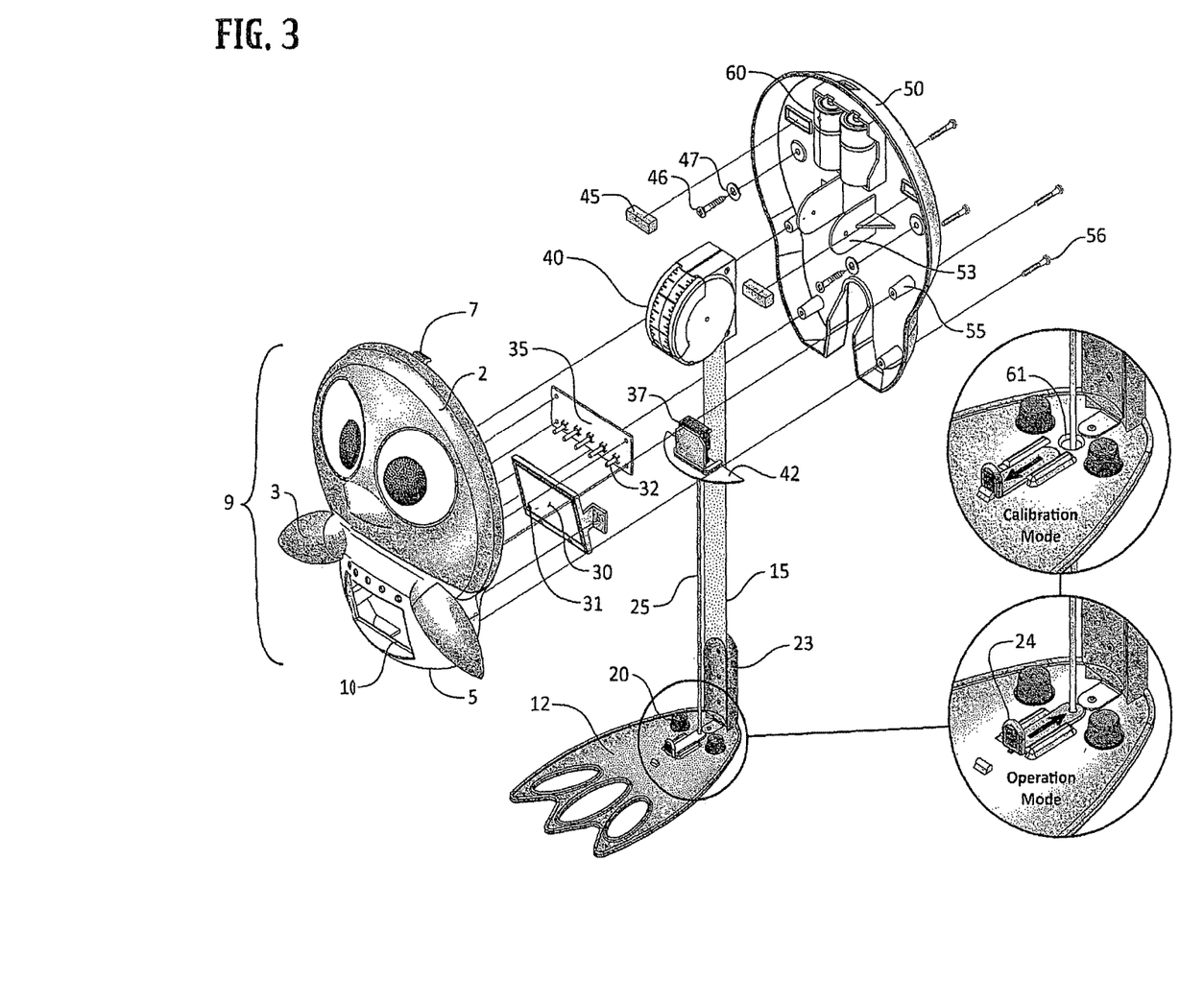
FIG. 3 is an exploded view of the height-measuring device having a laser sensor.

FIG. 3 is an exploded view of the height-measuring device [1], wherein a time-of-flight type laser device [37] is fixed onto a sensor bracket [42]. The laser device [37] captures height measurements of users or objects by means of a laser beam [25] reflecting off of the slider tab [24] in its closed position, which is located on the topside of the retractable foot platform [12]. The foot platform [12] has an aperture [61] positioned and hidden underneath the slider tab [24], and the slider tab [24] is closed during operation mode of the height-measuring device. Otherwise, the aperture [61] is exposed when the slider tab [24] is pulled away from the aperture [61], and is in its open position during calibration mode of the height-measuring device [1]. The retractable tape [15] is made from thin, rigid, but flexible material, and is preferably contained within a spring loaded tape housing [40]. In order to hold the tape housing [40] into place, it is inserted between walls [53], which protrude perpendicularly from the rear-facing shell [50]. When the foot platform [12] is pulled down vertically, the retractable tape [15] synchronously travels downward while the remaining length of the retractable tape [15] remains in a coiled state within the spring loaded tape housing [40]. As the retractable tape [15] extends, it exits from the tape housing [40], becoming uncoiled, and passes through a partially surrounding sensor bracket [42], which keeps the retractable tape [15] confined within a certain clearance. The retractable tape [15] and foot bracket [23] provides vertical parallelism and horizontal rigidity of the foot platform [12] along its travel path. The rear-facing shell [50] is configured to be mountable onto a surface, such as a wall, using mounting screws [46] and washers [47]. Bubble type or electronic level indicator [45] may be affixed within the housing, preferably onto the interior of the rear-facing shell [50], to ensure the height-measuring device [1] has the truest perpendicular wall mount with respect to the floor. The rear-facing shell [50] may attach to the front shell assembly [9] using one or more fasteners [56] through molded bosses [55]. The head [2] section attaches, or detaches, by means of one or more molded snap tabs [7], providing for a non-fastener access to the power supply/battery [60], as well as convenient access to the mounting screws [46] of the height-measuring device [1] itself.

A screen display [30] having an integrated camera [31] is incorporated into the front shell assembly [9] and is positioned adjacent to a corresponding Application Specific Integrated Circuit (ASIC) board [35]. The ASIC board [35] houses system hardware such as manual pushbuttons [32], processors, wireless radios, memory modules, voice recognition modules, face recognition modules, camera modules, microphones, audio speakers, and other electronics and microelectronics. Along with the manual pushbuttons [32], the screen display [30] may be used as a touch screen that enables the user to press buttons, add information, and/or manipulate objects using Graphic User Interface (GUI) buttons on the screen display [30]. Camera [31] may be used for face recognition and/or user, or object photographs. The height-measuring device [1] software accepts user inputs and/or object information, such as individual, or family member assignment, and can send data to the corresponding LED, LCD or similar screen display [30]. These options allow the user to easily input, initiate, manipulate, and/or associate user/object information, and password functionality.

Once the foot platform [12] is pulled downward and comes to rest atop of a user or object for a certain time, such as 3 seconds, the laser device [37] fires a downward directed laser beam [25] from its fixed mounting position on the sensor bracket [42] and reflects off of the foot platform's [12] slider tab [24]. Next, the laser device's [37] processor and algorithm instantaneously evaluate the time-of-flight data and output the precise travel distance of the plain retractable tape [15] and the adjoined foot platform [12]. Technologically, the laser device [37] heretofore is mentioned as being of the time-of-flight type, but may utilize triangulation, or any other technology that supports line-of-sight distance measurement.

Figure 4:
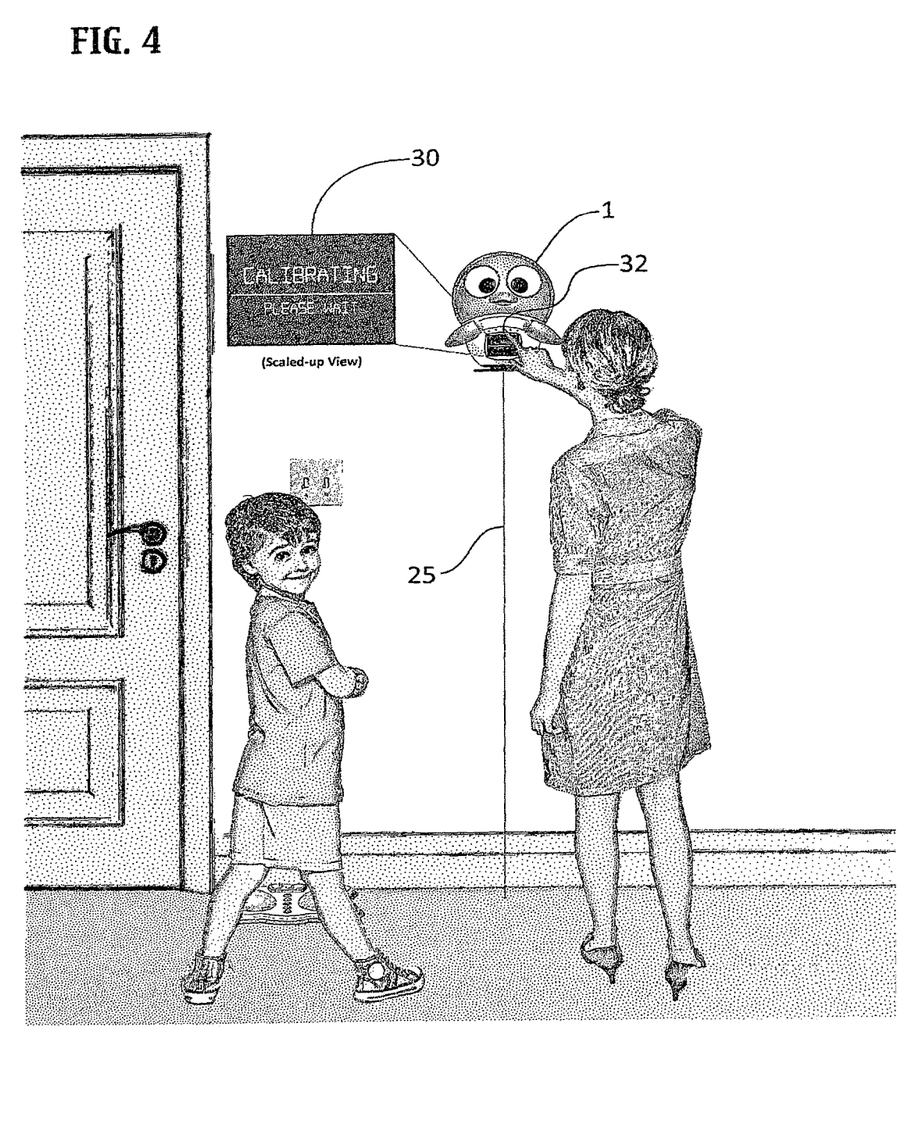
FIG. 4 is an illustrative view of the height-measuring device being calibrated using a laser method.

FIG. 4 depicts the height-measuring device [1] in calibration mode and illustrates the calibration process for the laser device [37]. After mounting the height-measuring device [1] onto a wall or other surface, the height-measuring device [1] should be calibrated electronically in order to record its relative position with respect to the floor or other surface. Referencing FIG. 3, the foot platform [12] has a slider tab [24], which perpendicularly extends, and is slidable across the aperture [61] allowing the user to open or close the aperture [61] and thereby control mode of operation of the height-measuring device [1]. During calibration mode, the foot platform [12] abuts the height-measuring device, and the slider tab [24] on the foot platform [12] automatically slides into an open position, or is manually slid open by the user. Once the slider tab [24] is open, the aperture [61] is exposed, and the laser beam [25] has a clear line of sight through the foot platform [12], and aperture [61], to the floor, or other surface. To initiate calibration, a pushbutton [32] is manually depressed for a certain period of time, such as 7 seconds, or the process may be activated via the touchscreen screen display [30], or by voice recognition. A concurrent audible beep may emit, while the laser beam [25] instantaneously passes through the aperture [61] and reflects off the floor, or other surface, transmitting the electronic distance signal back to the laser device [37] processor in order to capture and record the as-mounted calibration reading. The results of the calibration reading are stored in the ASIC board's [35] memory and may be displayed on the screen display [30], and/or alternately status information may be played from an audio speaker. Once the height-measuring device [1] is calibrated, the aperture [61] is either manually or automatically reclosed, and the height-measuring device [1] is now ready for use by individuals, or objects whose physical height is comfortably less than the calibrated as-mounted distance. No separate individualized calibration is necessary, but the height-measuring device [1] must be recalibrated if/when the vertical mounting position of height-measuring device [1] changes.

Figure 5:
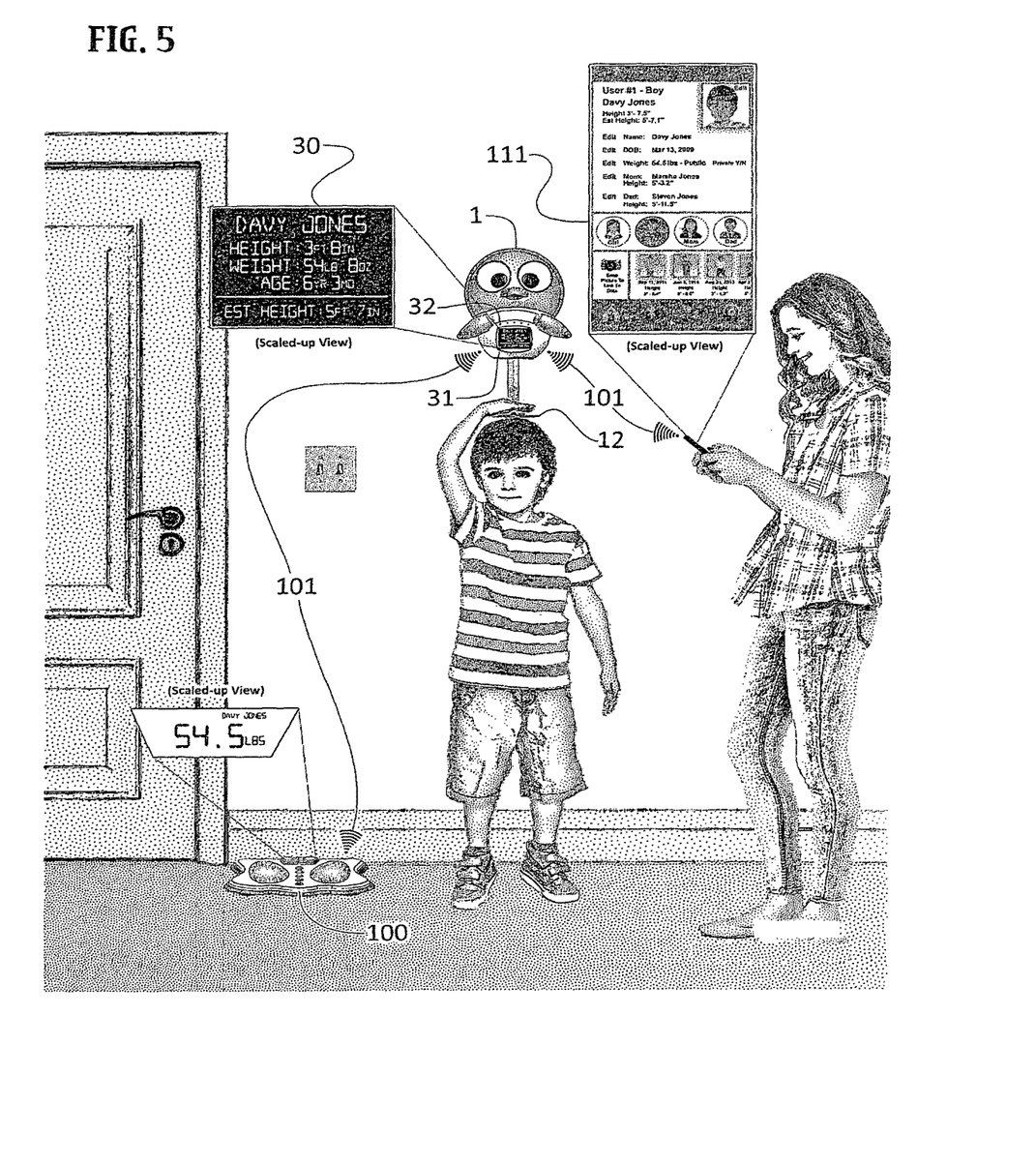
FIG. 5 is an illustrative view of the height-measuring device showing user engagement.

FIG. 5 illustrates the measurement process for a user who is positioned underneath the foot platform [12]. Given a certain setup protocol, the user may first program their personal pushbutton [32], which enables the height-measuring device [1] to recognize who is about to use the device [1], and then permanently correlates the user with the specific programmed pushbutton [32]. Likewise, the user selection of a personalized pushbutton [32] allows height measurements to be added to previously stored personal user data, not limited to previous height, weight, age, name, and gender. Alternately, the user could be automatically recognized via the integrated camera [31] using face recognition software capability.

In operation, the user simply depresses his/her personalized pushbutton [32], and within a certain timeframe, such as 10 seconds, the user pulls the foot platform [12], or it automatically travels downward until it abuts, and rests flatly on the crown of the user's head. Once the foot platform [12] comes to rest on user's head for a predetermined time, such as 3 seconds, an audible beep may emit, and the laser device [37] will automatically capture, and store in memory, the travel distance of the foot platform [12]. The total user or object height calculation is simply the difference between the stored as-mounted calibration distance, and the actual travel distance of the foot platform [12] as it comes to rest atop its target below. The ASIC board's system algorithm will cache, log, and save the digital height, and this data may be displayed on the screen display [30] and/or played from an audio speaker. Wired or wireless [101] data transmissions from the height measuring device [1] may be shared with a scale [100], a smart phone [111], or any other connected user device. Here, the height-measuring device's screen display [30] is not limited to displaying the user's first and last name, height, weight, age, estimated height, and/or photograph. Concurrently, the connected smart phone [111] is not limited to displaying shared data that may include the user's first and last name, current height, estimated future height, DOB, weight, gender, privacy settings, mother's name, mother's height, father's name, father's height, as well as user photographs, that are age, date, and height stamped. Similarly, the connected scale [100] is not limited to displaying the user's name, weight, and the like.

Figure 6:
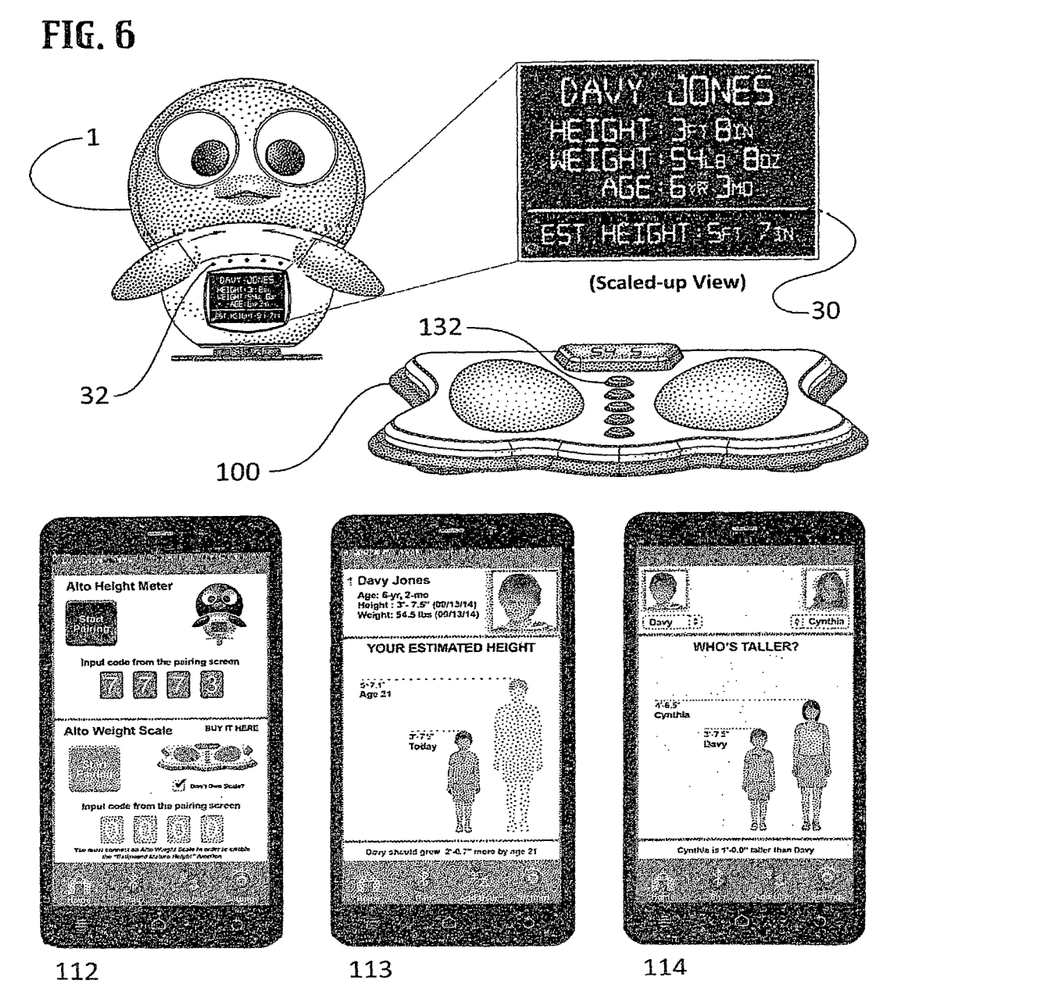
FIG. 6 is an illustrative view of the height-measuring device able to correspond to a smart application and/or scale.

FIG. 6 depicts the preferred system including the height-measuring device [1] connected to a proprietary weight scale [100] having shared data, memory, and foot-activated pushbuttons [132] corresponding to the height-measuring device's manual pushbuttons [32]. It also depicts smart phones [112], [113], and [114] which represent any number of connected possibilities such as tablets, monitors, personal computers, smart phones, or other devices. Smart phone [113] illustrates a screen, wherein the height-measuring device [1] is calculating, and displaying, a scaled graphical representation of a user's height juxtapose to a figure representing his/her comparative future height. Smart phone [114] illustrates a screen, wherein the height-measuring device [1] is calculating, and displaying, a scaled graphical representation of the user's height juxtapose to a comparative figure of a family member of equal, or different height. Smart phone [112] illustrates a screen in the process of receiving and/or transmitting pairing codes to the height-measuring device [1], and to the weight scale [100] respectively. Once all connected devices have been paired, and information synced and accumulated, the results may be displayed, shared, printed, and/or saved. The general scope of the height-measuring device's [1] data set includes, but is not limited to: personal information, sibling information, parent information, family tree data, medical records, demographic information, and other shared demographic API data.

The description of the disclosure has been presented for purposes of illustration and description, but is not intended to be exhaustive or limited in the form disclosed. It will be apparent to those of skill in the art that many modifications and variations are possible without departing from the scope and spirit of the disclosure, giving full cognizance to equivalents in all respects.

What is claimed:
1. A height measuring device, comprising:
a power supply contained within a housing;
said housing comprising:
  a front shell assembly and a rear-facing shell, wherein the front shell assembly is oriented in a direction opposite a mounting surface and wherein the rear-facing shell is oriented in a direction facing the mounting surface, such that the rear-facing shell is attached to the mounting surface via a fastener, and wherein the mounting surface is a wall within an environment comprising the wall, a ceiling and a floor;
  a display aperture with a screen display positioned within the display aperture, wherein the display aperture and the screen display are connected to one or more components that receive and store user input as well as a measured height of one or more objects;
  a laser sensor mounted onto a sensor bracket affixed within said housing, wherein the laser sensor is oriented such that the laser sensor is directed to the floor within the environment; and
  a retractable tape having two ends, wherein a first end is affixed within said housing, and wherein a second end is connected to a foot platform;
  said foot platform comprising:
    a first side having a surface that reflects a laser beam emitted from the laser sensor, and
    a second side having a surface that comes into contact with the one or more objects; and
    wherein the first side and the second side are fixedly attached to one another, in such a way that the first side is oriented in a direction toward the ceiling within the environment and the second side is oriented in a direction toward the floor within the environment; and
    wherein the surface that reflects the laser beam emitted from the laser sensor corresponds to a travel distance of said foot platform, in such a way that the travel distance of said foot platform extends to reach the one or more objects, indicating the measured height of the one or more objects;
  and wherein the foot platform further comprises:
    an aperture bored therethrough; and
    on the first side of the foot platform, a slider tab that, when moved into a first position, reveals the aperture and allows passing of the laser beam by transmission, and when moved into a second position, covers the aperture and prevents the laser beam from passing by reflection; and
    wherein the slider tab movement into the first and second positions is achieved by sliding the slider tab from one of the first and second positions to another of the first and second positions; and
    wherein the slider tab moved into the first position results in a calibration mode and wherein the slider tab moved into the second position results in an operation mode;
    wherein said calibration mode involves electronically capturing a height at which the height measuring device is mounted via the rear-facing shell by directing the laser beam emitted from the laser sensor through said aperture to the floor of the environment; and
    wherein said operation mode involves electronically capturing said foot platform travel distance by directing the laser beam emitted from the laser sensor onto the slider tab in the second position; and
  wherein said height measuring device electronically calculates the measured height of the one or more objects by subtracting said captured foot platform travel distance in said operation mode from said captured height in said calibration mode; and
  wherein said screen display displays the measured height of said one or more objects.
2. The height measuring device of claim 1, wherein said laser sensor outputs a plurality of distance measurements by interpreting a corresponding plurality of reflection signals reflected off of said slider tab on said foot platform.

3. The height measuring device of claim 1, wherein the retractable tape becomes uncoiled as the foot platform extends to reach the one or more objects.

4. The height measuring device of claim 1, wherein said rear-facing shell has at least one electronic level indicator ensuring a perpendicular mount on said mounting surface with respect to the floor within the room.

5. The height measuring device of claim 1, wherein said screen display is selected from a Group consisting of a touch screen, a smartphone, a tablet, a monitor, a camera, an audio speaker, and a scale.

6. The height measuring device of claim 1, wherein said one or more components is selected from a group consisting of at least one manual pushbutton, a processor, a wireless radio, a memory module, a voice recognition module, a face recognition module, a camera module, a microphone, and an audio speaker.

* * * * *